(12) United States Patent
Ribault et al.

(10) Patent No.: US 8,097,404 B2
(45) Date of Patent: Jan. 17, 2012

(54) COMPOSITION AND METHOD FOR CELL PERMEABILIZATION COMPRISING N-OCTYL-β-D-GLUCOPYRANOSIDE, SODIUM POLYPHOSPHATES, RUBIDIUM CHLORIDE AND/OR LITHIUM CHLORIDE FOR DETECTING LIVING CELLS ON A MEMBRANE

(75) Inventors: Sebastien Ribault, Romanswiller (FR); Frederic Olivieri, Barr (FR); Herve Meder, Strasbourg (FR); David Lehmann, Sundhoffen (FR); Sandra Laborde, Ottrott (FR)

(73) Assignee: Millipore Corporation, Billerica, MA (US)

( * ) Notice: Subject to any disclaimer, the term of this patent is extended or adjusted under 35 U.S.C. 154(b) by 490 days.

(21) Appl. No.: 12/383,277

(22) Filed: Mar. 20, 2009

(65) Prior Publication Data

US 2009/0246822 A1 Oct. 1, 2009

(30) Foreign Application Priority Data

Apr. 1, 2008 (FR) ..................... 08 52139

(51) Int. Cl.
*C12Q 1/00* (2006.01)
(52) U.S. Cl. .................. 435/4; 435/29; 435/34; 435/36
(58) Field of Classification Search ................ 435/4, 29, 435/34, 36
See application file for complete search history.

(56) References Cited

U.S. PATENT DOCUMENTS

2006/0134729 A1 6/2006 Besson-Faure et al.

FOREIGN PATENT DOCUMENTS

| FR | 2289984 A | * | 7/1976 |
| FR | 2 847 589 | | 5/2004 |
| GB | 1480992 A | | 7/1977 |
| WO | 96/14431 A1 | | 5/1996 |
| WO | 98/55861 A1 | | 12/1998 |
| WO | 01/59157 A2 | | 8/2001 |
| WO | 2004/050902 A1 | | 6/2004 |

OTHER PUBLICATIONS

English machine translation of FR 2847589 downloaded from the EPO Sep. 12, 2011.*
Denny et al. J. Microbiol. Immunol. Infect. (2001) 36: 72-76.*
Schulman, J. Annals NY Acad. Sci. (1966) 137(2): 860-863.*
The French Search Report dated Nov. 19, 2008.
The European communication dated May 14, 2009.
J.Pharm Pharmaceut Sci (www.cspsCanada.org) 9(1):32-39, 2006; Tirumalasetty, et al.; Permeability enhancing effects of the alkylglycoside, octylglucoside, on insulin permeation across epithelial membrane in vitro.—XP-002504629.
Journal of Antimicrobial Chemotherapy vol. 57 (2006), pp. 573-576, "In vitro antibacterial activities of tigecycline in combination with other antimicrobial agents determined by chequerboard and time-kill kinetic analysis", Peterson, et al.
International Journal of Food Microbiology, vol. 31 (1996) pp. 45-58, "Fluorogenic and chromogenic enzyme substrates in culture media and identification tests", Manafi.
The FASEB Journal, vol. 14, Jun. 2000, pp. 1041-1060, "Peptide nucleic acid (PNA): its medical and biotechnical applications and promise for the future", Ray, et al.
European Journal of Internal Medicine, Clinica Chimica Acta 363 (2006), pp. 48-60, "Real-time assays with molecular beacons and other fluorescent nucleic acid hybridization probes", Marras, et al.

* cited by examiner

*Primary Examiner* — Susan Hanley
(74) *Attorney, Agent, or Firm* — Nields, Lemack & Frame, LLC (57) ABSTRACT

The present invention relates to a composition for the permeabilization of the walls of microorganisms comprising the combination of octyl-β-D-glucopyranoside (NOG), sodium polyphosphates (HMP), and a salt chosen from lithium chloride or rubidium chloride, and a method for the enumeration and identification of cells on a membrane using said composition.

29 Claims, 3 Drawing Sheets

COMPOSITION AND METHOD FOR CELL PERMEABILIZATION COMPRISING N-OCTYL-β-D-GLUCOPYRANOSIDE, SODIUM POLYPHOSPHATES, RUBIDIUM CHLORIDE AND/OR LITHIUM CHLORIDE FOR DETECTING LIVING CELLS ON A MEMBRANE

PRIORITY CLAIMED

French Patent Application No 0852139 of Apr. 1, 2008

The present invention relates to a novel composition for cell permeabilization comprising the combination of N-octyl-β-D-glucopyranoside (NOG), sodium polyphosphates (HMP) and a salt chosen from rubidium chloride and lithium chloride, which makes it possible to label cells using fluorogenic markers while preserving the viability of said cells.

The invention also relates to a method for detecting and/or identifying living cells contained in a liquid or gaseous sample on a filtration membrane.

The invention applies more particularly to the microbiological quality control of liquid and gaseous media entering, for example, into the production chains for food or pharmaceutical products.

In this field, the contaminants may be present in various cellular forms, in particular Gram-positive or Gram-negative bacteria, diluted in large volumes of water or gas.

It is however not sufficient to merely detect these cells, it is also necessary to identify them precisely and to ensure that they are living cells in these media and not dead cells resulting from treatments to which the air or water may be subjected prior to their use. For example, a treatment of water with chlorine or ozone may leave dead cells in the medium which may be visually detected without as a result being a source of contamination.

Numerous methods of detection are described in the prior art for detecting within a limited time the presence of living cells in a liquid or gaseous medium on a filtration membrane. These methods generally comprise:
 a step of filtering said liquid or gaseous media through a filtration membrane;
 a step of incubating said membrane in contact with a nutrient medium for a few hours, during which the cells retained on the membrane by filtration divide so as to form microcolonies which are not visible to the naked eye; and
 a step of detecting cell clones forming the microcolonies by various luminescence or fluorescence techniques.

Such a method is described for example in application WO 01/59157. This method has been the subject of the development of a universal kit for the detection of living cells known by the name of "Milliflex Rapid" (Millipore). In this method, the step of detecting cells consists in lysing the filtered and incubated cells on the filtration membrane in order to release their adenosine triphosphate (ATP) content. The ATP released is used as a marker to identify and quantify the living cells (ATP-bioluminescence), which serves as a substrate for an enzyme (luciferase) capable of producing a chemiluminescence reaction. This chemiluminescence reaction gives rise to a light signal, which is captured through a video interface (CCD camera), and then restored in the form of a synthetic image. This synthetic image makes it possible to visualize in situ the site of the membrane where the microbe developed, in a manner similar to the conventional enumeration performed on a Petri dish in agar medium.

This technique has the advantage of universally detecting cells which are living because ATP is a molecule which exists in abundance in all living organisms. It thereby makes it possible to obtain a reliable indication of the number of contaminants present in the sample tested.

On the other hand, the extraction of ATP requires lysing, and therefore killing the cells, which does not make it possible to subsequently culture the microbes in order to characterize them, that is to say to determine their species.

The information obtained regarding the contamination is therefore of a quantitative and not of a qualitative nature.

Another method for detecting cells on a membrane is described in patent application FR 2 289 984. In this method, the step of detecting the cells retained on the filtration membrane is carried out using specific hybridization probes. The walls of the cells are made permeable to the detection probes by using a permeabilization composition combining Polyethyleneimine (PEI) and ethanol, and then, once these probes are inside the cells, the probes are specifically hybridized with genomic RNA or DNA sequences present inside the cells. These probes, which are generally of a polynucleotide nature, are selected so as to be able to specifically hybridize with nucleic acids so as to target one or more species of contaminants. The probes, which are labeled with a fluorescent or luminescent agent, are detected, after a washing step, using a camera which makes it possible to locate the cells on the membrane.

Although more specific, this method of detection does not make it possible to make a clear distinction between living cells and dead cells. Indeed, the hybridization of the probes may take place both in living and dead cells, and therefore leads to false positives. In addition, even though the permeabilization composition generally makes it possible to maintain the integrity of the wall of the cells, the method in its various steps does not make it possible to be able to maintain the cells alive because, in particular, of a step of fixing the cells on the cellulose membrane.

Application WO 2004/050902 describes another system of detection on a membrane which makes it possible to detect the presence of microorganisms contaminating blood samples. This method is designed to avoid causing the lysis of the microorganisms. The specific feature of this system lies in the fact that the detection of the microorganisms is carried out by the penetration of labeling agents into the microorganisms before filtration, while the microorganisms are still in a liquid medium. In this regard, the liquid sample to be tested is diluted in a permeabilization solution comprising the labeling agent and the permeabilization agent, before being filtered on the membrane and the cells detected.

The labeling agents used are small-sized molecules, in particular DNA intercalating compounds such as cyanine derivatives, propidium iodide, acridine orange or ethidium bromide. These compounds penetrate relatively easily across the wall of the microorganisms via the action of permeabilizing agents known to a person skilled in the art such as Polyethyleneimine (PEI), digitonin, nonensin, polymyxin or benzalkonium chloride. The intercalating agents become attached inside the nucleic acids during transcription or replication of the DNA, that is to say exclusively by the living cells contained in the sample.

This method makes it possible to universally label living cells while preserving the viability of the cells. However, the fact that the cells are labeled in a liquid medium before their filtration on a membrane introduces uncertainties regarding the final enumeration results obtained. Indeed, if the cells divide in a liquid phase while they are being labeled, the number of cells detected on the membrane may be twice that of the cells initially present. Moreover, the dilution of the liquid sample by the permeabilization and labeling composition introduces a significant margin of error into the final result, which margin of error is increased by the probability of an accidental contamination linked to the fluid handling operations necessary for carrying out the detection successfully.

In addition, in this situation, the labeled cells are filtered and detected individually on the membrane, that is to say cell by cell. The result is a detection signal which is low for each of the cells. This problem arises more particularly when fluorescent markers are used. Indeed, the membranes used, generally made of PVDF or of cellulose, themselves produce some fluorescence masking the weak fluorescence signal coming from the cells.

So-called "fluorogenic" markers have been developed over the past few years. These markers have the characteristic feature of emitting solely in the fluorescence region when they have been activated beforehand by an enzyme. These complex molecules generally comprise a fluorophore group capable of absorbing the light energy and of restoring this energy in the form of a characteristic fluorescence emission spectrum, and another group capable of masking or preventing the fluorescence of said fluorophore from manifesting itself. The enzyme has the effect of modifying this second group so that the fluorescence of the first can be detected.

These fluorescent markers are found to be particularly useful for the counting of viable cells by cytometry as is described, for example, in application WO 98/55861. However, as this application underlines, cells labeled with fluorogenic agents have a fluorescence signal which is often too weak to be detected separately on a membrane, which is similar to the problems encountered above with the DNA intercalating agents which are fluorescent.

Application WO 96/14431 describes a technique for detecting microorganisms and more particularly the detection of coliform bacteria, based on the capacity of these Gram-negative bacteria to produce enzymes having the possibility to activate the fluorogenic markers: β-glucuronidase and β-galactosidase. The corresponding fluorogenic substrates used are methylumbelliferyl-β-D-galactopyranoside (MU-Gal), 4-trimethylfluoromethyl-umbelliferyl-β-D-galactopyranoside (TFMU-gal) and 4-tri-methylfluoromethylumbelliferyl-β-D-glucoronide (TFMUG). This technique is based on the same principle as the methods described above, where the liquid or gaseous sample in which the coliform bacteria exist is first filtered, and then the bacteria are incubated on the filtration membrane, and then the microcolonies formed are detected with the aid of the above fluorogenic substrates.

However, this technique has certain limitations.

The first of these limitations is that the method of detection is only applicable to certain Gram-negative bacteria (coliforms) synthesizing β-glucuronidase and β-galactosidase.

A second limitation is that the quantity of β-glucuronidase and β-galactosidase produced by the cells is generally too low to obtain a detectable signal. It is therefore necessary, in order to reach a satisfactory sensitivity, to treat the cells with a synthetic inducer of the expression of β-glucuronidase and β-galactosidase such as isopropyl-beta-thiogalactoside (IPTG).

Another limitation, on which the intensity of the detected signal directly depends, relates to the penetration of the fluorogenic markers into the cells. This penetration is made difficult because of the size of the markers and the fact that said fluorogenic markers have a tendency to be released from the cells by efflux mechanisms.

To increase the penetration of the markers into the cells, the prior art teaches using cell permeabilizing agents such as the antibiotics polymyxin B and colistin in combination with lysozyme and incubating the cells at 40° C. However, this permeabilization, while it may prove sufficient for coliform bacteria, is far from being satisfactory for Gram-positive bacteria such as $Staphylococcus\ aureus$, which is a pathogenic agent that is searched for. In addition, the use of antibiotic agents such as polymyxin B and colistin as permeabilizing agent does not make it possible to maintain the viability of the bacteria [Petersen J. P. et al. (2006) J. Antimicrobial. Chem. 57: 573-576].

The abovementioned method therefore not only remains limited to the detection of coliform bacteria but does not make it possible to keep the cells alive.

Consequently, the prior art methods do not make it possible to satisfactorily meet the double requirement of a quantitative information useful for evaluating the number of cells in the medium derived from different species (universal detection of living cells) and a qualitative information which makes it possible to characterize said species which are present.

It therefore remains necessary to be able to have permeabilizing compositions having a broad spectrum, that is to say which make it possible to permeabilize a large number of species of cells of various types without being too aggressive towards those which are more fragile.

It is well known, for example, that Gram-positive microorganisms, which possess a single membrane having a thick outer layer consisting of peptidoglycans (polymer consisting of peptide and polysaccharide chains) do not exhibit the same organization as Gram-negative bacteria, whose wall consists of a more fragile double membrane, in which the peptidoglycans are less abundant and more dispersed, and that consequently the permeabilization of these two types of microorganisms at the same time is difficult to carry out.

The aim of the present invention is to address the limitations of the existing detection systems mentioned above, in particular as regards the permeabilization of Gram-positive and -negative bacteria as a whole in the context of the fluorescence labeling of living cells.

Surprisingly, the inventors have observed that the combination of NOG, HMP and rubidium chloride and/or lithium chloride made it possible to obtain, on a membrane, satisfactory permeabilization of Gram-positive and -negative bacteria.

This permeabilization has the advantage of preserving the viability of the detected cells, and thus of being able to carry out the subsequent culture of the detected cells, in particular for the purpose of their characterization.

The present invention emphasizes the importance of combining, in effective quantities, NOG, which is a known permeabilizing agent, with HMP, which is a powerful detergent, which would have been expected to have a destructive rather than protective action on the cell walls.

The present invention also emphasizes that the use of rubidium chloride and lithium chloride makes it possible to substantially improve the efficacy of the permeabilization compositions comprising the combination of NOG and HMP.

The permeabilization composition which is the subject of the present invention allows, more particularly, the use of a method for labeling cells on a membrane with the aid of fluorogenic compounds or probes.

A: colonies of cells permeabilized with composition No. 11 and comprising no rubidium chloride.

B: colonies of cells permeabilized with composition No. 12 according to the invention, comprising rubidium chloride.

It is apparent on these photographs that composition No. 12 allows a clearer detection of the cells than composition No. 11.

A: colonies of cells permeabilized with composition No. 11 according to the invention containing no rubidium chloride.

B: colonies of cells permeabilized with composition No. 12 comprising rubidium chloride.

It is evident from this analysis that the fluorescence is more intense and better localized when composition No. 12 according to the invention which comprises rubidium chloride is used.

A first aspect of the invention consists of a composition for cell permeabilization useful for causing the penetration of macromolecules into a cell.

A macromolecule is a complex molecule resulting from the assembly, by covalent bonds, of several similar or different chemical groups, such as proteins, nucleic acids, polysaccharides, whose molecular weight is generally greater than 1000 daltons and most often greater than 5000 daltons.

A cell is defined here as a small-sized biological entity comprising a cytoplasm delimited by a membrane and containing genetic material in the form of nucleic acids.

The term microorganism relates, for the purposes of the present invention, to a cell having a microscopic size, that is to say a size of between 0.5 and 5 microns, having a metabolic and reproductive potential, such as algae, unicellular fungi, protozoa, mycetes, bacteria or gametes.

The microorganisms searched for are more particularly pathogenic Gram-positive or -negative bacteria of the genera *Pseudomonas, Escherichia, Legionella, Salmonella, Listeria, Bacillus, Streptococcus, Vibrio, Yersinia, Staphylococcus, Mycobacterium, Shigella, Clostridium, Campylobacter*, or *Aeromonas*; protozoa of the genera *Giardia, Entamoeba, Cryptosporidium, Cyclospora*; mycoplasmas of the genera *Mycoplasma* and *Ureaplasma*; fungi of the genera *Saccharomyces, Aspergillus, Candida* or *Penicillium*.

The aim of the invention is more particularly to cause the penetration of so-called fluorogenic markers into cells while preserving the viability of said cells.

The viability of cells is determined, for the purposes of the present invention, by the capacity of said cells to divide after transfer of the cells onto a nutrient medium.

A fluorogenic marker, for the purposes of the present invention, is a macromolecule comprising a fluorophore group capable of absorbing light energy and restoring this energy in the form of a characteristic fluorescence emission spectrum. The fluorophore group is situated in the macromolecule such that the fluorescence emission at the expected wavelength is conditioned by a change in the configuration of the macromolecule by the action of a specific enzyme. In general, the enzyme which allows this activation has an esterase activity aimed at a specific bond in the macromolecule. It is therefore a fluorescence marker which can only be detected in the presence of a specific enzyme. This enzyme is present in the cell, which implies the need for the cell to be alive in order to be labeled.

Two types of fluorogenic marker can be distinguished according to the invention: fluorogenic compounds and fluorogenic probes.

Fluorogenic compounds are fluorogenic markers as defined above. They allow the detection of any living cell into which they penetrate, provided that the enzyme which allows their activation is present therein. These fluorogenic compounds are preferably chosen from the following: FDA (fluoroscein diacetate), 6-CFDA (6-carboxyfluorescein diacetate), 5-CFDA, 5/6-CFDA, 5-maleimide FDA, fluorescein dilaurate, fluorescein dibutyrate, 5(6)2',7'-dichloro-CFDA, 5(6)-sulfo-FDA, 5(6)2',7'-dichloro-FDA, 5,6-CFDA-N-hydroxysuccinimide ester, fluorescein dipropionate, di-beta-D-galactoside fluorescein, 3-o-methylfluorescein phosphate, pentaacetoxy ester of 2',7'-bis(carboxyethyl)-5(6)-carboxyfluorescein (BCECF/AM), azidofluorescein diacetate, chloromethylfluorescein diacetate, eosin diacetate, carboxyeosin diacetate, 4-methylumbelliferyl acetate, 4-methylumbelliferyl beta-D-galactoside, 4-methylumbelliferyl alpha-D-mannopyranoside, 4-methylumbelliferyl nonanoate, 4-methylumbelliferyl phosphate, methyl-1-umbelliferylglucoromide, alanine-7-amino-4-methylcoumarin, glycine-7-amino-4-methylcoumarin, proline-7-amino-4-methylcoumarin, valine-7-amino-4-methylcoumarin, glycyl-L-proline-7-amino-4-methylcoumarin, 1,4-diacetoxy-2,3-dicyanobenzene (ABD), hydroethidine, resorufin acetate.

These compounds are well known to a person skilled in the art [Manafi, M., Fluorogenic and chromogenic enzyme substrates in culture media and identification tests (1996) *Journal of Food Microbiology* 31: 45-58].

Fluorogenic probes are compounds combining a fluorogenic compound, preferably one of those listed above, with a probe allowing a specific detection by hybridization of nucleic acids contained in the cells. The most common specific probes comprise an oligonucleotide fragment having a length generally between 10 and 40 nucleotides forming a sequence complementary to that contained in a DNA or an RNA of the microorganism. A preferred target RNA for this type of probes is the 16S RNA of the cell, which generally comprises sequences specific to the pathogenic microorganisms commonly searched for.

Probes of the PNA (peptide nucleic acids) type may also constitute advantageous probes in this type of detection because they have a peptide backbone that is less sensitive to the degradation enzymes present in the cells [Arghya et al., Peptide nucleic acid (PNA): its medical and biotechnical applications and promise for the future (2000) *The FASEB Journal*. 14: 1041-1060].

Generally, the fluorogenic probes are designed such that the fluorescence emission is dependent on the fact that the probe is specifically hybridized with its target, or else on the fact that the probe has been integrated into the cell genome during its replication.

These probes often comprise a quencher, that is to say a second fluorophore group absorbing the fluorescence of the first fluorophore in the absence of hybridization or of integration of the probe into the genome of the cell. Such probes, such as the probes Beacon™, are known to a person skilled in the art [Salvatore A. E. et al., Real time assays with molecular beacons and other fluorescent nucleic acid hybridization probes (2005) *European journal of internal medicine*].

The use of fluorogenic markers for detecting cells, in particular in the context of microbiology on a membrane, has several limitations recalled above, in particular the difficulty of causing the penetration of these molecules, which are generally large in size, in a sufficient number, without permanently damaging the cell walls.

The present invention succeeds in overcoming this problem by providing a composition comprising:
- a final concentration (weight volume) of at least 0.01% of N-octyl-β-D-glucopyranoside (NOG);
- a final concentration (weight volume) of at least 0.1% of sodium polyphosphates (HMP); and
- a final concentration (moles per liter) of at least 1 mmol·l$^{-1}$ of rubidium chloride and/or lithium chloride.

It is evident from the various experiments presented in the experimental part of the present application that NOG, HMP and lithium or ribidium chloride, taken in combination, result in a permeabilization composition which makes it possible to detect a broad spectrum of microorganisms with the aid of fluorogenic markers, both Gram-positive bacteria and Gram-negative bacteria.

This composition has the surprising effect of allowing the penetration of the fluorogenic markers without killing the cells, such that it is possible to culture them after the detection step.

N-Octyl-β-D-glucopyranoside ($C_{14}H_{28}O_6$) (CAS: 29836-26-8) is a membrane protein solubilizing agent known in the prior art to have a permeabilizing effect on Gram-negative bacteria. However, as the results below show, it is considered to be unsuitable for permeabilizing Gram-positive bacteria.

Preferably, the final concentration of NOG is between about 0.03 and 0.2%, more preferably between about 0.05 and 0.2% by total weight of the composition.

Sodium polyphosphate (HMP) is a mixture of salts based on sodium polymetaphosphate of general composition $(NaPO_3)_6$ (CAS 50813-16-6). These salts are prepared by melting mono-orthophosphates followed by an abrupt cooling. The result is a crystalline structure that is highly soluble in water (Calgon S) which is hydrolyzed in the form of sodium trimetaphosphate and sodium orthophosphate. HMP is used as dispersing agent and detergent. It can sometimes, in this capacity, enter into compositions for cell permeabilization. However, compositions containing it are aggressive for the cells, which does not make it possible to preserve the viability of the cells. As the results below show, the use of HMP alone is not satisfactory as regards the permeabilization of Gram-negative bacteria.

The final concentration of HMP is generally between 0.1% and 2% by weight, more generally between about 0.5% and 1.5% by weight, preferably greater than 1%.

Lithium chloride (LiCl) and rubidium chloride (RbCl) are salts that are not widely used in microbiology because they are generally attributed the same properties as sodium chloride (NaCl), which is a lot cheaper and whose use is a lot more widespread.

However, surprisingly, lithium chloride and rubidium chloride make it possible, in the context of the present invention, and in very different proportions, to obtain a better detection of the fluorogenic compounds, in particular in the case of the labeling of microcolonies on a membrane. The use of these salts makes it possible to obtain in particular a better clarity of the signal intercepted by the fluorescence detector. This effect, which is perceptible on the synthetic image presented in FIG. 3, could result from a lower diffusion of the fluorogenic markers around the microcolonies linked to the fact that the walls of the cells are made less fragile. As shown in FIG. 4, the comparison of the fluorescence distribution profiles at the level of the microcolonies reveals a higher and better localized fluorescence intensity at the level of the labeled cells.

Preferably, the final concentration of rubidium chloride is between about 1 and 20 mmol·l$^{-1}$. Where appropriate, the final concentration of rubidium chloride is between about 10 and 15 mmol·l$^{-1}$.

Preferably, the final concentration of lithium chloride is between about 0.5 and 2 mol·l$^{-1}$, more preferably between about 1 and 2 mol·l$^{-1}$.

As the mixture of the two salts proved optimal in the experiments described, the permeabilization composition, according to a preferred aspect of the invention, comprises lithium chloride and rubidium chloride in the form of a mixture. The ratio between the lithium chloride and the rubidium chloride in this mixture is preferably between 10 and 1000, preferably between 50 and 200.

The reasons why the combination of these compounds: NOG, HMP and a salt chosen from lithium chloride and rubidium chloride, proves particularly appropriate for permeabilizing the walls of both Gram-positive bacteria and Gram-negative bacteria are not exactly known.

According to a preferred aspect of the invention, the permeabilization composition as defined above is in solution in water, an MOPS, MES or HEPES buffer. It is indeed advantageous for the composition to contain no buffer of the PBS type (Phosphate Buffer Solution). It was found that PBS-type buffer solutions were not compatible with a number of fluorogenic compounds, such as CFDA or FDA, which are the preferred fluorogenic markers according to the invention.

The composition according to the invention may comprise at least one fluorogenic marker as defined above. However, the fluorogenic marker may also be stored separately and may be applied directly, being incorporated for example into a so-called labeling solution, at the time of detection of the permeabilized cells.

The invention relates in particular to the use of a permeabilization composition as defined above, in a method for the enumeration and/or identification of cells.

Said composition is particularly advantageous for the detection of fluorescent living cells (by fluorescence?), in particular when it is sought to simultaneously detect various types of cell, in particular both Gram-positive and -negative microorganisms.

The subject of the invention is thus more particularly a method for the enumeration and/or identification of living cells on a membrane, characterized in that it comprises the following steps:
a) one or more living cells are deposited on a membrane;
b) the cells deposited on the membrane are brought into contact with a permeabilization composition according to any one of claims 1 to 9;
c) the permeabilized cells are brought into contact, simultaneously or subsequently, with one or more fluorogenic markers capable of crossing the wall of the microorganisms;
d) the markers which have penetrated inside the microorganisms are detected by fluorescence.

In general, the cells in step a) are deposited on the membrane by filtration of a liquid or gaseous medium, through said membrane, in which the cells are initially present.

The expression liquid or gaseous medium is understood here to mean any fluid which may be filtered by applying a pressure difference across a membrane having pores with a mean diameter generally between 0.1 and 1.5 microns, and preferably between 0.15 and 0.8 micron, more preferably between 0.2 and 0.6 micron. Such a fluid may consist of pure solutions entering into the manufacture of sterile products but also of complex solutions such as drinking water, beverages, medical fluids (serum, urine, amniotic fluid and the like).

The present method may therefore have applications in the diagnostic field for the analysis of liquid samples obtained from animals or patients.

The expression "membrane" denotes in the present application a synthetic support having two sides, whose pores have a known mean diameter.

The membrane used in the context of the present invention generally has a high surface/volume ratio and a constant thickness preferably between 10 and 200 microns.

Such a membrane may be in the form of the mono- or multilayer. It generally consists of one or more materials chosen from polytetrafluoroethylene, poly(vinylidene)fluoride (PVDF), polycarbonate, polyamide, polyester, polyethersulfone, acetylcellulose and nitrocellulose.

The materials are preferably chosen so as to be compatible with the solvents used, in particular alcohols and aldehydes capable of being used in the various steps of the method.

The membrane on which the microorganisms are detected preferably mainly consists of PVDF (polyvinylidene fluoride) or Nylon®. More preferably, it is a PVDF membrane filter of the type marketed by the company Millipore® under the trade name Milliflex and the references MXHVWP124 or RMHVMFX24. The filtration, if it takes place, may be performed for example by means of Millipore® filtration modules known by the name of "Milliflex®".

Once the microorganisms have been filtered and retained on the membrane, an optional step of culturing the microorganisms in contact with an appropriate culture medium may be included in the method between steps a) and b). This culture medium is preferably an agar medium on which the membrane is deposited after filtration. This step, which is optional, makes it possible to obtain colonies of each of the microorganisms initially filtered, which increases the number of cells to be detected.

According to the invention, the microorganisms are then brought into contact in step b) with a permeabilization composition according to the invention as described above. This step is preferably produced in a small volume of solution forming a film at the surface of the membrane. Alternatively, the permeabilization composition may be contained in a solid support on which the membrane will be deposited, such as for example an impregnated pad or an agar, which limits the possible displacements of liquid at the surface of the membrane and therefore the mixing of the microorganisms. It is performed at a temperature between 20° C. and 45° C. for a duration of about 5 to 60 minutes.

In step c), depending on the cases, the fluorogenic markers are incorporated into the permeabilization composition, or alternatively the permeabilized cells are brought into contact with said markers subsequently, that is to say by bringing the cells into contact with a labeling solution comprising said markers. The permeabilization composition is then diluted or replaced by the labeling solution.

When the fluorogenic markers consist of specific probes, it is possible to detect in a targeted manner some types of cell or microorganism, depending on the choice of probes.

Step d) of detection is carried out by a measurement of fluorescence with the aid of a fluorescence sensor performed under standard conditions. The fluorescence is generally captured by a CCD camera in a dark chamber which makes it possible, with an image processing software, to measure the light energy emitted by the fluorogenic compounds.

The method according to the invention is advantageous in that it allows a detection of the cells performed directly on the membrane, the cells being alive. This method therefore allows culturing of the detected cells, at the end of the detection step d), in an appropriate culture medium, in particular for the purpose of carrying out a more complete characterization of the microorganisms tested. It is thus possible to verify the cellular species present.

Another aspect of the invention consists of kits which make it possible to carry out the abovementioned method for the detection and/or enumeration of cells. Such a kit generally comprises a composition for the permeabilization of the cell walls as defined above and optionally an additional component such as a fluorogenic marker or a filtration membrane.

Preferably, the filtration membrane is a membrane mainly consisting of cellulose, polyvinylidene fluoride (PVDF) or polyethersulfone.

The examples which follow are aimed at illustrating the invention without any limitation thereto.

EXAMPLES 1.1 Fluorescence Detections Performed with the Aid of Various Permeabilization Compositions The tested strains of *E. coli* (Gram-negative bacterium) ATCC 8739 and of *S. aureus* (Gram-positive bacterium) ATCC 6538 or *B. subtilis* (Gram-positive bacterium) ATCC 6633 were preserved in cryotubes (Dutscher, ref. 028049) frozen at −80° C. prepared from freeze-dried strains obtained from collections.

For the manufacture of the cryotubes, a 100 ml bottle of TS broth (Biomérieux, ref. 41146) is inoculated on the day of the preparation of the tubes and incubated at 35-37° C. For the growth, measurements of OD at 600 nm are performed at regular intervals with the aid of a spectrophotometer (Eppendorf, Biophotometer ref. 6131 000.012). Growth is stopped when the OD reaches 0.5. Into each cryotube, 600 μl of cryoprotectant (Sigma, cell freezing with glycerol, ref. C6039) and 600 μl of culture are distributed. The tubes are mixed and then placed at −80° C.

Enumeration of the broth and of a nonfrozen cryotube is performed by plating $10^{-5}$ and $10^{-6}$ dilutions. These dilutions are prepared in 9 ml bottles of peptone water (Biomérieux, ref. 42111). 100 μl of each dilution is plated with a scraper on a TSA agar (Biomérieux, ref. 43011) incubated for 24 hours at 35° C. The operation is repeated three times. The next day, the cryotube is thawed and enumerated in the same manner. An API gallery (Biomérieux) allows the identification and the confirmation of the purity of the cryotubes prepared.

For all the tests, the bacteria strains are diluted in tubes of peptone water (Biomérieux, ref. 42111). A cascade dilution is performed by adding 1 ml of the cryotube of the strain used to 9 ml of the tube of peptone water until the desired dilution is obtained. The concentration was adjusted in order to obtain on average 30 bacteria per sample. This concentration was verified on a Petri dish by a conventional count test on agar medium.

The filtration is carried out with the aid of the Milliflex Plus Vacuum pump (Millipore, ref. MXP PLUS01) in Milliflex funnels with a cellulose ester or PVDF membrane having a porosity of 0.45 μm (Millipore, ref. MXHVWP124). The bacteria are added to 50-100 ml of physiological saline 0.9% NaCl (B. Braun, ref. 0066570 E).

The membranes are incubated on cassettes of solid media Milliflex Trypcase-soy agar (Millipore, ref. MXSM CTS48) or R2A (Millipore, ref. MXSM CRA 48) in an incubator at 32.5° C.+/−2.5° for a time necessary for the microorganisms to form microcolonies.

After incubation, the membranes are separated from the agar medium and brought into contact with 2 ml of permeabilization solution on a sealed support (absorbent pads of the cassettes for Millipore liquid medium, ref. MXLM CO120) for 30 minutes at room temperature or at 35° C.

The following permeabilization solutions were tested:

| Composition No. 1: | |
|---|---|
| NaAc | 50 mM |
| LiCl | 1.13 M |
| RbCl | 10 mM |
| Water | |

| Composition No. 2: | |
|---|---|
| NaAc | 50 mM |
| NOG | 0.10% |
| Water | |

| Composition No. 3: | |
|---|---|
| NaAc | 50 mM |
| HMP | 1% |
| Water | |

| Composition No. 4: | |
|---|---|
| NaAc | 50 mM |
| LiCl | 1.13 M |
| RbCl | 10 mM |
| NOG | 0.10% |
| Water | |

| Composition No. 5: | |
|---|---|
| NaAc | 50 mM |
| LiCl | 1.13 M |
| RbCl | 10 mM |
| HMP | 1% |
| Water | |

| Composition No. 6: | |
|---|---|
| NaAc | 50 mM |
| NOG | 0.10% |
| HMP | 1% |
| Water | |

| Composition No. 7: | |
|---|---|
| NaAc | 50 mM |
| LiCl | 1.13 M |
| RbCl | 10 mM |
| NOG | 0.10% |
| HMP | 1% |
| Water | |

| Composition No. 8: | |
|---|---|
| LiCl | 1.13 M |
| RbCl | 10 mM |
| NOG | 0.10% |
| HMP | 1% |
| HEPES buffer | 20 mM |

| Composition No. 9: | |
|---|---|
| LiCl | 1.13 M |
| RbCl | 10 mM |
| NOG | 0.10% |
| HMP | 1% |
| MOPS buffer | 0.1 M |

| Composition No. 10: | |
|---|---|
| LiCl | 1.13 M |
| RbCl | 10 mM |
| NOG | 0.10% |
| HMP | 1% |
| Water | |

| Composition No. 11: | |
|---|---|
| NaAc | 50 mM |
| NaCl | 1.13 M |
| NOG | 0.10% |
| HMP | 1% |
| Water | |

| Composition 12: | |
|---|---|
| NaAc | 50 mM |
| RbCl | 10 mM |
| NOG | 0.10% |
| HMP | 1% |
| Water | |

A universal fluorogenic marker, namely 5/6-carboxyfluorescein diacetate (CFDA) (Sigma 21879-100MG) diluted in DMSO, is added to the permeabilization compositions in order to reach a final concentration of 100 μg/ml. The membrane remains in contact with the marker substrate for 30 minutes at 35° C. The membrane is then removed from the labeling solution and placed in an illuminator equipped with a camera in order to measure the fluorescence emitted between 520 and 530 nm.

The fluorescence intensity results summarized in Tables 1 to 3 below correspond to the light energy (luminescence) captured and recorded to the nearest pixel by the CCD camera using the Sherlock image analyzing software (Insosys Inc.). The values indicated are the absolute photometric values (ratio of luminescence between luminescence measured and background noise) on a scale between 0 and 255. The software is parameterized such that the value 0 corresponds to the fluorescence of the membrane alone in the absence of cells. The margin of error of the measurements is estimated at ±1.5. The various permeabilization compositions mentioned correspond to compositions 1 to 7 of which the details are given above.

TABLE 1

Summary of compositions 1 to 7 tested

| | Compositions | | | | | | |
|---|---|---|---|---|---|---|---|
| | 1 | 2 | 3 | 4 | 5 | 6 | 7 |
| NaAc | 50 mM | 50 mM | 50 mM | 50 mM | 50 mM | 50 mM | 50 mM |
| LiCl | 1.13M | / | / | 1.13M | 1.13M | / | 1.13M |
| RbCl | 10 mM | / | / | 10 mM | 10 mM | / | 10 mM |
| NOG | / | 0.10% | / | 0.10% | / | 0.10% | 0.10% |
| HMP | / | / | 1% | / | 1% | 1% | 1% |
| Water | Water | Water | Water | Water | Water | Water | Water |

TABLE 2

Fluorescence intensities measured for compositions 1 to 7

| | Compositions | | | | | | |
|---|---|---|---|---|---|---|---|
| | 1 | 2 | 3 | 4 | 5 | 6 | 7 |
| E. coli | 0 | 0 | 0 | 45 | 0 | 0 | 46 |
| S. aureus | 45 | 58 | 37 | 0 | 58 | 38 | 33 |

TABLE 3

Fluorescence intensities measured for compositions 8 to 10

| No. | Permeabilization composition | Fluorescence intensity S. aureus (Gram+) | Fluorescence intensity E. coli (Gram−) |
|---|---|---|---|
| | Cellulose ester membrane | 0 | 0 |
| 8 | LiCl: 1.13 M<br>RbCl: 10 mM<br>NOG: 0.10%<br>HMP: 1%<br>Hepes buffer: 20 mM | 24.8 | 40.4 |
| 9 | LiCl: 1.13 M<br>RbCl: 10 mM<br>NOG: 0.10%<br>HMP: 1%<br>MOPS buffer: 0.1 M | 31.9 | 51.6 |
| 10 | LiCl: 1.13 M<br>RbCl: 10 mM<br>NOG: 0.10%<br>HMP: 1%<br>Buffer: water | 24.9 | 44.4 |

TABLE 4

Rate of recovery of the various microorganisms treated with composition No. 7

| Microorganism | ATCC | Recovery (%) | Recovery viability (%) |
|---|---|---|---|
| Escherichia coli | 8739 | 100 | 122 |
| Bacillus subtilis | 6633 | 104 | 104 |
| Staphylococcus aureus | 6538 | 102 | 111 |
| Salmonella enterica | 13314 | 117 | 117 |
| Pseudomonas aeruginosa | 9027 | 111 | 96 |

1.2 Interpretation of the Results

Figure 1:
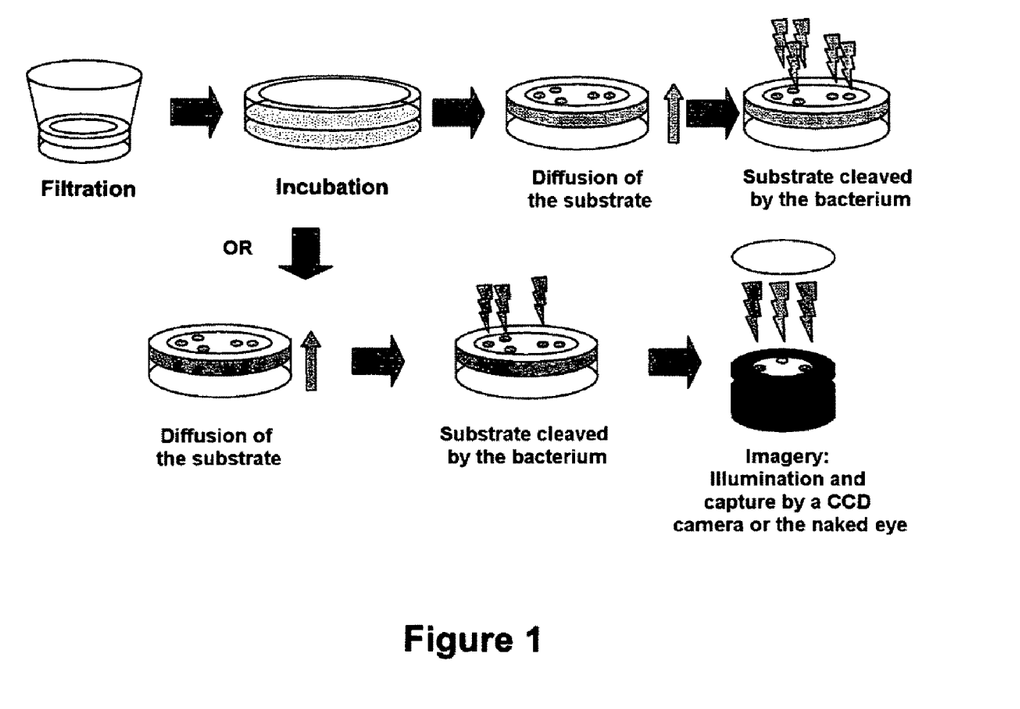
FIG. 1: Principle of the detection of the fluorescence labeled cells according to the method of the invention.
Figure 2:
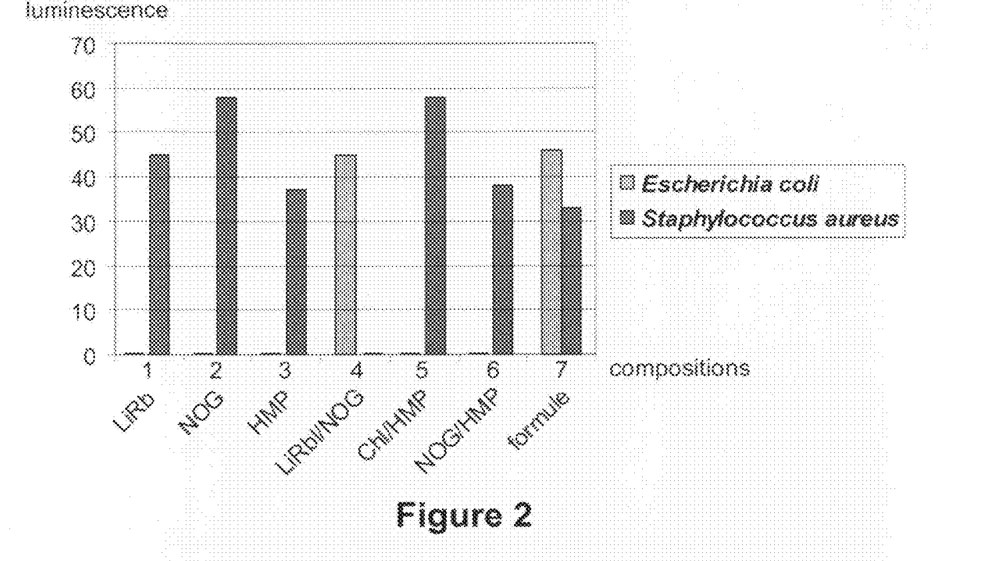
FIG. 2: Representation in diagrammatic form of the detection results obtained with the aid of compositions 1 to 7 summarized in Table 1. The y-axis indicates the mean fluorescence intensity obtained for each composition used. The x-axis juxtaposes said compositions, each having being tested for *E. coli* and *S. aureus*. The expressions LiRb, NOG, HMP, LiRb/NOG, Chl/HMP, NOG/HMP and formula correspond to compositions 1 to 7, respectively, summarized in Table 1.

The comparative results obtained with compositions 1 to 7 (FIG. 2 and Table 2) show that the combination of HMP, NOG and rubidium and/or lithium chloride in the same permeabilization composition (composition 7 according to the invention) makes it possible to obtain a satisfactory detection both of E. coli (Gram−) and of S. aureus (Gram+).

The results obtained with compositions 8, 9 and 10 show that the buffers without phosphates MOPS, MES or HEPES are quite suitable for the compositions according to the invention, just like water, and can replace the PBS buffer used in the prior art.

Figure 3:
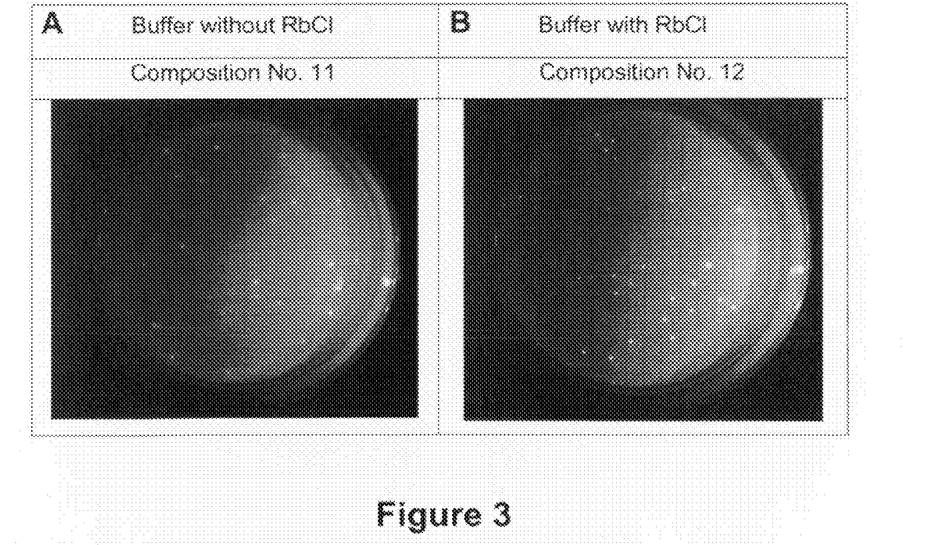
FIG. 3: Photograph of microcolonies made fluorescent by labeling with 5/6-CFDA after permeabilization of the cells (*E. coli* ATCC 8739) by composition Nos. 11 and 12.
Figure 4:
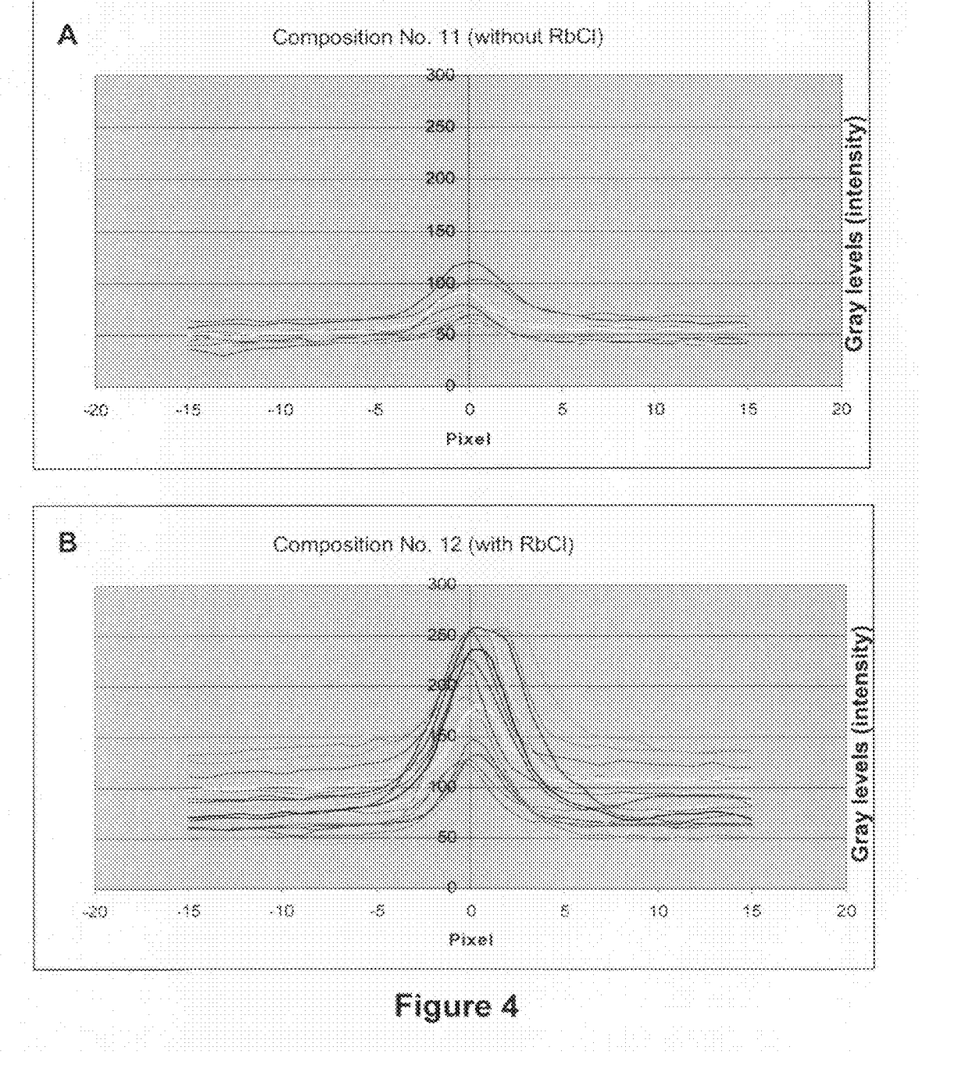
FIG. 4: Topological distribution of the fluorescence intensity around the colonies treated with composition Nos. 11 and 12.

The use of compositions 11 and 12, illustrated in FIGS. 3 and 4, suggests a positive effect of rubidium chloride on the intensity and the location of the fluorescence. FIG. 3, which is a photograph, shows a better clarity of the labeling when the cells are treated with composition 12 according to the invention. This effect is perceptible to the naked eye (by means of a filter which makes it possible to better visualize the fluorescence). FIG. 4 gives the fluorescence intensity differences obtained when localized measurements are carried out at the level of the labeled microcolonies.

The recovery results reported in Table 4 above, which correspond to the number of viable bacteria at the end of the treatment of the cells with composition 7 according to the invention compared with the same cells not treated, indicate that the viability of the cells is preserved regardless of the microorganisms used (Gram+ and Gram−).

The invention claimed is:

1. A composition for bacterial cell permeabilization which causes penetration of a fluorogenic marker into a living bacterial cell while preserving the viability of said living bacterial cell, comprising:
   a final concentration (weight volume) of at least 0.01% of N-octyl-β-D-glucopyranoside (NOG);
   a final concentration (weight volume) of at least 0.1% of sodium polyphosphates (HMP); and
   a final concentration of at least 1 mmol·l$^{-1}$ of rubidium chloride and/or lithium chloride.

2. The composition according to claim 1, comprising lithium chloride.

3. The composition according to claim 1, comprising rubidium chloride.

4. The composition according to claim 1, comprising a mixture of lithium chloride and rubidium chloride.

5. The composition according to claim 1, wherein the final concentration of HMP is between 0.1% and 2% by weight volume.

6. The composition according to claim 1, wherein the final concentration of HMP is greater than 1% by weight volume.

7. The composition according to claim 1, wherein the final concentration of NOG is between 0.03 and 0.2% by weight volume.

8. The composition according to claim 1, comprising rubidium chloride in a final concentration between 1 and 20 mmol·l$^{-1}$.

9. The composition according to claim 1, comprising lithium chloride in a final concentration between 0.5 and 2 mol·l$^{-1}$.

10. The composition according to claim 1, wherein said composition is in solution in water or in an MOPS, MES or HEPES buffer.

11. The composition according to claim 1, wherein said composition does not comprise Phosphate Buffer Solution (PBS).

12. The composition according to claim 1, further comprising at least one fluorogenic marker.

13. The composition according to claim 12, wherein said fluorogenic marker is a fluorogenic probe.

14. The composition according to claim 12, wherein said fluorogenic marker is selected from the group consisting of: fluorescein diacetate (FDA), 6-carboxyfluorescein diacetate (6-CFDA), 5-carboxyfluorescein diacetate (5-CFDA), 5/6-CFDA, 5-maleimide FDA, fluorescein dilaurate, fluorescein dibutyrate, 5(6)-2',7'dichloro-CFDA, 5 (6)-sulfo-FDA, 5(6)-2',7'-dichloro-FDA, 5(6)-CFDA-N-hydroxysuccinimide ester, fluorescein dipropionate, di-beta-D-galactoside fluorescein, 3-o-methylfluorescein phosphate, pentaacetoxy ester of 2',7'-bis(carboxyethyl)-5(6)-carboxyfluorescein (BCECF/AM), pentaacetoxy ester of 2',7'-bis(carboxyethyl)-5(6)-fluorescein (BCECF/AM), azidofluorescein diacetate, chloromethylfluorescein diacetate, eosin diacetate, carboxyeosin diacetate, 4-methylumbelliferyl acetate, 4-methylumbelliferyl beta-D-galactoside, 4-methylumbelliferyl alpha-D-mannopyranoside, 4-methylumbelliferyl nonanoate, 4-methylumbelliferyl phosphate, methyl-1-umbelliferylglucoromide, alanine-7-amino-4-methylcoumarin, glycine-7-amino-4-methylcoumarin, prolinevaline-7-amino-4-methylcoumarin, glycyl-L-proline-7-amino-4-methylcoumarin, 1,4-diacetoxy-2,3-dicyanobenzene acetate (ABD), hydroethidine, and resorufin acetate.

15. The composition according to claim 12, wherein said fluorogenic marker is CFDA or FDA or a derivative of CFDA or FDA.

16. A method for the enumeration and/or identification of living bacterial cells on a membrane wherein the bacterial cells each comprise a cell wall, comprising the following steps:
   a) depositing the living bacterial cells on a membrane;
   b) contacting the living bacterial cells deposited on the membrane with a permeabilization composition comprising:
      a final concentration (weight volume) of at least 0.01% of N-octyl-β-D-glucopyranoside (NOG);
      a final concentration (weight volume) of at least 0.1% of sodium polyphosphates (HMP); and
      a final concentration of at least 1 mmol·$l^{-1}$ of rubidium chloride and/or lithium chloride;
   c) simultaneously or subsequently contacting the permeabilized living bacterial cells on the membrane with one or more fluorogenic markers capable of crossing the cell walls the living bacterial cells; and
   d) detecting by fluorescence the one or more markers which have penetrated inside the living bacterial cells.

17. The method according to claim 16, wherein the living bacterial cells in step a) are initially present in a liquid or gaseous medium and are deposited on the membrane by filtration of the liquid or gaseous medium through said membrane.

18. The method according to claim 16 or 17, wherein between step a) and step b) the living bacterial cells on the membrane are cultured such that the living bacterial cells deposited in step a) are present in step b) in the form of microcolonies of living bacterial cells.

19. The method according to claim 16, wherein said fluorogenic marker used in step c) is a fluorogenic probe.

20. The method according to claim 19, wherein said fluorogenic probe is a hybridization probe.

21. The method according to claim 16, wherein said fluorogenic marker used in step c) is selected from the group consisting of: fluorescein diacetate (FDA), 6-carboxyfluorescein diacetate (6-CFDA), 5-carboxyfluorescein diacetate (5-CFDA), 5/6-CFDA, 5-maleimide FDA, fluorescein dilaurate, fluorescein dibutyrate, 5(6)-2',7'dichloro-CFDA, 5(6)-sulfo-FDA, 5(6)-2',7'-dichloro-FDA, 5(6)-CFDA-N-hydroxysuccinimide ester, fluorescein dipropionate, di-beta-D-galactoside fluorescein, 3-O-methylfluorescein phosphate, pentaacetoxy ester of 2',7'-bis(carboxyethyl)-5(6)-carboxyfluorescein (BCECF/AM), pentaacetoxy ester of 2',7'-bis(carboxyethyl)-5(6)-fluorescein (BCECF/AM), azidofluorescein diacetate, chloromethylfluorescein diacetate, eosin diacetate, carboxyeosin diacetate, 4-methylumbelliferyl acetate, 4-methylumbelliferyl beta-D-galactoside, 4-methylumbelliferyl alpha-D-mannopyranoside, 4-methylumbelliferyl nonanoate, 4-methylumbelliferyl phosphate, methyl-1-umbelliferylglucoromide, alanine-7-amino-4-methylcoumarin, glycine-7-amino-4-methylcoumarin, prolinevaline-7-amino-4-methylcoumarin, glycyl-L-proline-7-amino-4-methylcoumarin, 1,4-diacetoxy-2,3-dicyanobenzene acetate (ABD), hydroethidine, and resorufin acetate.

22. The method according to claim 21, wherein said fluorogenic marker is CFDA or FDA or a derivative of CFDA or FDA.

23. The method according to claim 16, wherein the detection in step d) is carried out with a fluorescence sensor.

24. The method according to claim 16, wherein the membrane on which the living bacterial cells are deposited comprises cellulose, polyvinylidene fluoride (PVDF) or polyethersulfone.

25. The method according to claim 16, wherein the membrane on which the living bacterial cells are deposited has a mean pore diameter 1.5 microns.

26. The method according to claim 16, wherein the living bacterial cells thus detected are cultured after step d).

27. A kit for the detection and/or enumeration of living bacterial cells each having a cell wall, comprising:
   a) at least one fluorogenic marker; and
   b) a composition for the permeabilization of the cell walls comprising:
      a final concentration (weight volume) of at least 0.01% of N-octyl-p-D-glucopyranoside (NOG);
      a final concentration (weight volume) of at least 0.1% of sodium polyphosphates (HMP); and
      a final concentration of at 1 mmol·$l^{-1}$ of rubidium chloride and/or lithium chloride.

28. A kit for the detection and/or enumeration of cells, comprising:
   a) a filtration membrane; and
   b) a composition for the permeabilization of the cell walls comprising:
      a final concentration (weight volume) of at least 0.01% of N-octyl-β-D-glucopyranoside (NOG);
      a final concentration (weight volume) of at least 0.1% of sodium polyphosphates (HMP); and
      a final concentration of at least 1 mmol·$l^{-1}$ of rubidium chloride and/or lithium chloride.

29. The kit according to claim 28, wherein said filtration membrane comprises cellulose, polyvinylidene fluoride (PVDF) or polyethersulfone.

* * * * *